United States Patent

Kluender et al.

[11] Patent Number: 5,863,915
[45] Date of Patent: Jan. 26, 1999

[54] SUBSTITUTED 4-ARYLBUTYRIC ACID DERIVATIVES AS MATRIX METALLOPROTEASE

[75] Inventors: Harold C. E. Kluender, Trumbull; Brian R. Dixon, Woodbridge; David R. Brittelli, Branford, all of Conn.

[73] Assignee: Bayer Corporation, Pittsburgh, Pa.

[21] Appl. No.: 857,004

[22] Filed: May 15, 1997

Related U.S. Application Data

[60] Provisional application No. 60/051,008 May 15, 1996.
[51] Int. Cl.[6] .................. C07D 209/48; C07C 59/84; C07C 59/90; A61K 31/19
[52] U.S. Cl. .................. 514/243; 514/248; 514/367; 514/373; 514/375; 514/568; 544/183; 544/237; 548/165; 548/169; 548/209; 548/221; 548/226; 548/473; 548/480; 562/459
[58] Field of Search ............ 514/243, 248, 514/367, 373, 375, 568; 544/183, 237; 548/165, 169, 209, 221, 226, 473, 480; 562/459

[56] References Cited

U.S. PATENT DOCUMENTS 5,459,131  10/1995  Albright et al. ............. 514/19
5,684,152  11/1997  Ponpipom et al. ............ 544/242

FOREIGN PATENT DOCUMENTS 1068751  5/1967  United Kingdom ............ C07C 39/12
1565616  4/1980  United Kingdom ............ C07C 63/52

OTHER PUBLICATIONS

Chem. Abstract 112:56713, 1990.

*Primary Examiner*—Mukund J. Shah
*Assistant Examiner*—Deepak R. Rao

[57] ABSTRACT

Inhibitors for matrix metalloproteases, pharmaceutical compositions containing them, and a process for using them to treat a variety of physiological conditions. The compounds of the invention have the generalized formula

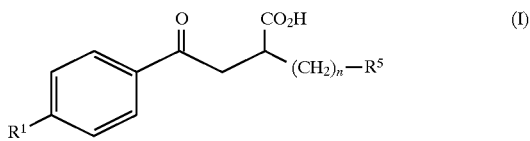

wherein $R^1$ represents $C_6$–$C_{12}$ alkyl; $C_5$–$C_{12}$ alkoxy; $C_5$–$C_{12}$ alkylthio; a polyether of formula $R^2O(C_2H_4O)_a$— in which a is 1 or 2 and $R^2$ is $C_1$–$C_5$ alkyl, phenyl, or benzyl; and substituted alkynyl of formula $R^3(CH_2)_b$—C≡C—; in which b is 1–10 and $R^3$ is H—, HO—, or $R^4O$— in which $R^4$ is $C_1$–$C_3$ alkyl, phenyl, or benzyl. The alkyl, phenyl, and benzyl portions of $R^1$ may bear at least one pharmaceutically-acceptable substituent. The subscript n is 2–4. $R^5$ represents phenyl; imidoyl of 4–12 carbon atoms; (3H)-benzo-1,2,3-triazin-4-on-3-yl; N-saccharinyl; (2H)-phthalazin-1-on-2-yl; 2-benzoxazolin-2-on-3-yl; 5,5-dimethyloxazolidine-2,4-dion-3-yl; and thiazolidine-2,4-dion-3-yl; with the phenyl and benzo portions of $R^5$ permissibly bearing at least one pharmaceutically-acceptable substituent. Pharmaceutically acceptable salts of these materials are also included.

13 Claims, No Drawings

SUBSTITUTED 4-ARYLBUTYRIC ACID DERIVATIVES AS MATRIX METALLOPROTEASE

This application claims priority from U.S. provisional application 60/051,008, filed May 15, 1996.

FIELD

This invention relates to enzyme inhibitors, and more particularly, to novel 4-arylbutyric acid derivatives useful for inhibiting matrix metalloproteases.

BACKGROUND

The matrix metalloproteases (also known as matrix metalloendoproteinases or MMPs) are a family of zinc endoproteinases which include, but are not limited to, interstitial collagenase (also known as MMP-1), stromelysin (also known as proteoglycanase, transin, or MMP-3), gelatinase A (also known as 72 kDa-gelatinase or MMP-2) and gelatinase B (also known as 95 kDa-gelatinase or MMP-9). These MMPs are secreted by a variety of cells including fibroblasts and chondrocytes, along with natural proteinatious inhibitors known as TIMPs (Tissue Inhibitor of MetalloProteinase).

All of these MMPs are capable of destroying a variety of connective tissue components of articular cartilage or basement membranes. Each MMP is secreted as an inactive proenzyme which must be cleaved in a subsequent step before it is able to exert its own proteolytic activity. In addition to the matrix destroying effect, certain of these MMPs such as MMP-3 have been implicated as the in vivo activator for other MMPs such as MMP-1 and MMP-9 (Ito, A.; Nagase, H. Arch. Biochem. Biophys. 267, 211–6 (1988); Ogata, Y.; Enghild, J. J.; Nagase, H. J. Biol. Chem. 267, 3581–4 (1992)). Thus, a cascade of proteolytic activity can be initiated by an excess of MMP-3. It follows that specific MMP-3 inhibitors should limit the activity of other MMPs that are not directly inhibited by such inhibitors.

It has also been reported that MMP-3 can cleave and thereby inactivate the endogenous inhibitors of other proteinases such as elastase (Winyard, P. G.; Zhang, Z.; Chidwick, K.; Blake, D. R.; Carrell, R. W.; Murphy, G. FEBS Lett. 279, 91–4 (1991)). Inhibitors of MMP-3 could thus influence the activity of other destructive proteinases by modifying the level of their endogenous inhibitors.

A number of diseases are thought to be mediated by excess or undesired matrix-destroying metalloprotease activity or by an imbalance in the ratio of the MMPs to the TIMPs. These include: a) osteoarthritis (Woessner, J. F., Jr.; Selzer, M. G. J. Biol. Chem. 259, 3633–8 (1984) and Phadke, K. J. Rheumatol. 10, 852–60 (1983)), b) rheumatoid arthritis (Mullins, D. E.; Rohrlich, S. T. Biochim. Biophys. Acta 695, 117–214 (1983), Woolley, D. E.; Crossley, M. J.; Evanson, M. J. Arthritis Rheum. 20, 1231–9 (1977), and Gravallese, E. M.; Darling, J. M.; Ladd, A. L.; Katz, J. N.; Glimcher, L. H. Arthritis Rheum. 34, 1076–84 (1991)), c) septic arthritis (Williams, R. J., III; Smith, R. L.; Schurman, D. J. Arthritis Rheum. 33, 533–41 (1990)), d) tumor metastasis (Reich, R.; Thompson, E. W.; Iwamoto, Y.; Martin, G. R.; Deason, J. R.; Fuller, G. C.; Miskin, R. Cancer Res. 48, 3307–12 (1988) and Matrisian, L. M.; Bowden, G. T.; Krieg, P.; Fuerstenberger, G.; Briand, J. P.; Leroy, P.; Breathnach, R. Proc. Natl. Acad. Sci. U.S.A. 83, 9413–7 (1986)), e) periodontal diseases (Overall, C. M.; Wiebkin, O. W.; Thonard, J. C. J. Peridontal. Res. 22, 81–8 (1987)), f) corneal ulceration (Burns, F. R.; Stack, M. S.; Gray, R. D.; Paterson, C. A. Invest. Ophthalmol. Vis. Sci. 30, 1569–75 (1989)), g) proteinuria (Baricos, W. H.; Murphy, G.; Zhou, Y.; Nguyen, H. H.; Shah, S. V. Biochem. J. 254, 609–12 (1988)), h) coronary thrombosis from atherosclerotic plaque rupture (Davies, M. J.; Foster, K.; Hembry, R.; Murphy, G.; Humphries, S. Proc. Natl. Acad. Sci. U.S.A. 88, 8154–8) (1991)), i) aneurysmal aortic disease (Vine, N.; Powell, J. T. Clin. Sci. 81, 233–9 (1991)), j) birth control (Woessner, J. F., Jr.; Morioka, N.; Zhu, C.; Mukaida, T.; Butler, T.; LeMaire, W. J. Steroids 54, 491–9 (1989)), k) dystrophobic epidermolysis bullosa (Kronberger, A.; Valle, K. J.; Eisen, A. Z.; Bauer, E. A. J. Invest. Dermatol. 79, 208–11 (1982)), and l) degenerative cartilage loss following traumatic joint injury, conditions leading to inflammatory responses, osteopenias mediated by MMP activity, tempero mandibular joint disease, demyelating diseases of the nervous system, etc. (Chantry, A.; Earl, C.; Groome, N.; Glynn, P. J. Neurochem. 50, 688–94 (1988)).

The need for new therapies is especially important in the case of arthritic diseases. The primary disabling effect of osteoarthritis (OA), rheumatoid arthritis (AR) and septic arthritis is the progressive loss of articular cartilage and thereby normal joint function. No marketed pharmaceutical agent is able to prevent or slow this cartilage loss, although nonsteroidal antiinflammatory drugs (NSAIDs) have been given to control pain and swelling. The end result of these diseases is total loss of joint function which is only treatable by joint replacement surgery. MMP inhibitors are expected to halt or reverse the progression of cartilage loss and obviate or delay surgical intervention.

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiments with various types of proteases have shown that the matrix metalloproteases, in particular, gelatinases A and B (MMP-2 and MMP-9, respectively) play a dominant role in these processes. For an overview of this field see Mullins, D. E.; Rohrlich, S. T. Biochim. Biophys. Acta 695, 177–214 (1983), Ray, J. M.; Stetler-Stevenson, W. G. Eur. Respir. J. 7, 2062–72 (1994) and Birkedal-Hansen, H.; Moore, W. G. I.; Bodden, M. K.; Windsor, L. J.; Birkedal-Hansen, B.; DeCarlo, A.; Englar, J. A. Crit. Rev. Oral. Biol. Med. 4, 197–250 (1993).

Furthermore, it could be shown that inhibition of degradation of extracellular matrix by the native matrix metalloprotease inhibitor TIMP-2 (a protein) arrests cancer growth (De Clerck, Y. A.; Perez, N.; Shimada, H.; Boone, T. C.; Langley, K. E.; Taylor, S. M. Cancer Res. 52, 701–8 (1992)) and that TIMP-2 inhibits tumor-induced angiogenesis in experimental systems (Moses, M. A.; Sudhalter, J.; Langer, R. Science 248, 1408–10 (1990)). For a review see De Clerck, Y.; Shimada, H.; Taylor, S. M.; Langley, K. E. Ann. N. Y. Acad. Sci. 732, 222–32 (1994). It was also demonstrated that the synthetic matrix metalloprotease inhibitor batimastat when given intraperitoneally inhibits human colon tumor growth and spread in an orthotopic model in nude mice (Wang, X.; Fu, X.; Brown, P. D.; Crimmin, M. J.; Hoffman, R. M. Cancer Res. 54, 4726–8 (1994)) and prolongs the survival of mice bearing human ovarian carcinoma xenografts (Davies, B.; Brown, P. D.; East, N.; Crimmin, M. J.; Balkwill, F. R. Cancer Res. 53, 2087–91 (1993)). The use of this and related compounds has been described in WO-A-9321942.

There are several patents and patent applications disclosing the use of metalloproteinase inhibitors for the retardation of metastatic cancer, promoting tumor regression, inhibiting cancer cell proliferation, slowing or preventing of cartilage loss associated with osteoarthritis or for treatment of other diseases as indicated above (e.g. WO-A-9519965, WO-A-9519956, WO-A-9519957, WO-A-9519961, WO-A-9321942, WO-A-9321942, WO-9421625, U.S. Pat. No. 4,599,361; U.S. Pat. No. 5,190,937; EP 0574 758 A1, published Dec. 22, 1993; EP 026 436 A1 published Aug. 3, 1988; and EP 0520 573 A1, published Dec. 30, 1992). The preferred compounds of these patents have peptide backbones with a zinc complexing group (hydroxamic acid, thiol, carboxylic acid or phosphinic acid) at one end and a variety of side chains, both those found in the natural amino acids as well as those with more novel functional groups. Such small peptides are often poorly absorbed, exhibiting low oral bioavailability. They are also subject to rapid proteolytic metabolism, thus having short half lives. As an example, batimastat, the compound described in WO-A-9321942, can only be given intraperitoneally.

It would be desirable to have effective MMP inhibitors which possess improved bioavailabilty and biological stability relative to the peptide-based compounds of the prior art, and which can be optimized for use against particular target MMPs. Such compounds are the subject of the present application.

SUMMARY

This invention relates to compounds having matrix metalloprotease inhibitory activity and the generalized formula:

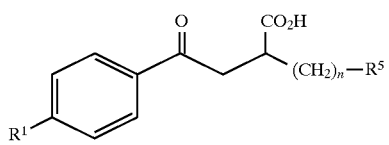

wherein
$R^1$ represents a substituent independently selected from the group consisting of
$C_6$–$C_{12}$ alkyl;
$C_5$–$C_{12}$ alkoxy;
$C_5$–$C_{12}$ alkylthio;
polyether of formula $R^2O(C_2H_4O)_a$—; wherein
a is 1 or 2; and
$R^2$ is $C_1$–$C_5$ alkyl, phenyl, or benzyl; and
substituted alkynyl of formula $R^3(CH_2)_b$—C≡C—; wherein
b is 1–10; and
$R^3$ is H—, HO—, or $R^4$O—, wherein
$R^4$ is $C_1$–$C_3$ alkyl, phenyl, or benzyl;
alkyl, phenyl, and benzyl portions of $R^1$ permissibly bearing at least one pharmaceutically-acceptable substituent;
the subscript n is 2–4;
$R^5$ represents a substituent independently selected from the group consisting of
phenyl;
imidoyl of 4–12 carbon atoms;
(3H)-benzo-1,2,3-triazin-4-on-3-yl
N-saccharinyl;
(2H)-phthalazin-1-on-2-yl;
2-benzoxazolin-2-on-3-yl;
5,5-dimethyloxazolidine-2,4-dion-3-yl; and
thiazolidine-2,4-dion-3-yl;
phenyl and benzo portions of $R^5$ permissibly bearing at least one pharmaceutically-acceptable substituent;
and pharmaceutically acceptable salts thereof.

In addition to the above-described compounds, the invention also relates to pharmaceutical compositions having matrix metalloprotease inhibitory activity, which compositions comprise a compound of the invention as described above and in more detail in the detailed description below, and a pharmaceutically acceptable carrier.

The invention also relates to a method for treating a matrix metalloprotease-mediated condition in a mammal to achieve an effect, comprising administering to the mammal an amount of a compound of the invention as described above and in more detail in the detailed description below, which is effective to treat the condition.

DETAILED DESCRIPTION

The matrix metalloprotease-inhibiting compounds of the invention include the 4-phenylbutyric acid derivatives having the generalized formula (I) shown above.

$R^1$ may be a straight or branched, or cyclic alkyl group of 6–12 carbon atoms, preferably of 7–11 carbon atoms, and optionally may bear one or more pharmaceutically-acceptable substituents which are discussed more fully below. Any branching or substitution is preferably located at least three chain atoms away from the point of attachment of the $R^1$ group to the phenyl ring.

$R^1$ may also be an alkoxy or alkylthio group containing a straight, branched or cyclic alkyl group of 5–12 carbon atoms, preferably 6–10 carbon atoms. This alkyl group optionally may bear one or more pharmaceutically-acceptable substituents which are discussed more fully below. Any branching or substitution is preferably located three or more carbons from the point of attachment of the $R^1$ group to the phenyl ring.

R1 may also be a polyether of the formula $R^2O(C_2H_4O)_a$— in which the subscript "a" is 1 or 2, and the group $R^2$ is a straight, branched or cyclic alkyl group of 1–5 carbon atoms, preferably of 1–3 carbon atoms, or phenyl, or benzyl. $R^2$ optionally may bear one or more pharmaceutically-acceptable substituents which are discussed more fully below. Any branching or substitution is preferably located at least three chain atoms away from the point of attachment of the polyether group $R^1$ to the phenyl ring.

R1 may also be a substituted alkynyl group of the formula

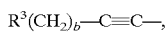

in which the subscript "b" is 1–10, and the group $R^3$ is H—, HO—, or $R^4$O—, and preferably the HO— group. $R^4$ may be an alkyl group of 1–3 carbon atoms, or phenyl, or benzyl. $R^3$ optionally may bear one or more pharmaceutically-acceptable substituents which are discussed more fully below.

The subscript n in formula (1) represents the number of methylene units in the chain bearing substituent $R^5$, and is 2–4, but preferably 2–3.

The group $R^5$ may be:
phenyl,
imidoyl of 4–12 carbon atoms,
(3H)-benzo-1,2,3-triazin-4-on-3-yl of formula (3H)-benzo-1,2,3-triazin-4-on-3-yl of formula

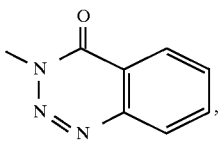

N-saccharinyl of formula

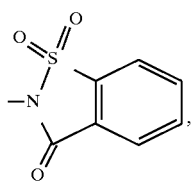

(2H)-phthalazin-1-on-2-yl of formula

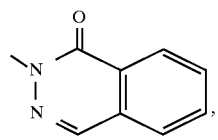

2-benzoxazolin-2-on-3-yl of formula

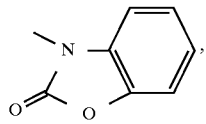

5,5-dimethyloxazolidine-2,4-dion-3-yl of formula

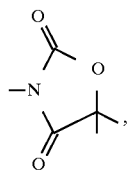

and thiazolidine-2,4-dion-3-yl of formula

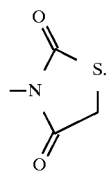

Preferably, $R^5$ is phthalimidoyl or the (3H)-benzo-1,2,3-triazin-4-on-3-yl group shown above. In substituent $R^5$, the phenyl or benzo rings may optionally may bear one or more pharmaceutically-acceptable substituents which are discussed more fully below.

Possible substituents include the following: halogen, lower alkyl, haloalkyl, —CN, —NO$_2$, —CO$_2$R$^6$, —OCOR$^6$, CH$_2$OR$^6$, —CONR$^6$R$^7$, —COR$^6$, and —OR$^8$. In these formulae R$^6$ represents H or lower alkyl; R$^7$ represents H or lower alkyl; or R$^6$ and R$^7$ together with the nitrogen to which they are attached form a morpholine ring; and R$^8$ represents H, lower alkyl or haloalkyl. The term lower alkyl is defined as a straight or branched alkyl group of 1–4 carbon atoms. Haloalkyl is defined as a lower alkyl group substituted by 1–3 halogen atoms which may be the same or different.

In addition to the compounds of formula (I) discussed above, the invention also encompasses analogs of these materials which include a 4- or 5-membered ring structure (not shown in formula (I)) which contains the carbon atoms numbered 2 and 3 of the parent butyric acid, and may include some or all of the alkylene chain bearing group $R^5$. These ring-containing compounds are shown in figure (I') below,

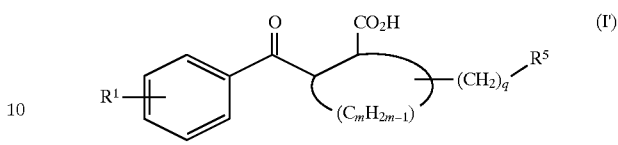

in which m is 2–3; q is 0–2 and $R^1$ and $R^5$ are as defined above.

Those skilled in the art will appreciate that many of the compounds of the invention exist in enantiomeric or diastereomeric forms, and that it is understood by the art that such stereoisomers generally exhibit different activities in biological systems. This invention encompasses all possible stereoisomers which possess inhibitory activity against an MMP, regardless of their stereoisomeric designations, as well as mixtures of stereoisomers in which at least one member possesses inhibitory activity.

The most preferred compounds of the present invention are as indicated and named in the list below:

4-(4-(3-hydroxyprop-1-ynyl)phenyl)-4-oxo-2-(3-phenylpropyl)butyric acid

4(4(hex-1-ynyl)phenyl)-4-oxo-2-(3-phenylpropyl)butyric acid 4-(4-(6hydroxyhex-1-ynyl)phenyl)-4-oxo-2-(3-phenylpropyl)butyric acid 4-(4-(hex-1-ynyl)phenyl)-4-oxo-2-(2-phthalimidoethyl)butyric acid 4-(4-(6-hydroxyhex-1-ynyl)phenyl)-4-oxo-2-(2-phthalimidoethyl)butyric acid 4-(4-(3-hydroxyprop-1-ynyl)phenyl)-4-oxo-2-(2-phthalimidoethyl)butyric acid 4-(4-hexylphenyl)-4-oxo-2-(2-phthalimidoethyl)butyric acid 4-(4-(dec-1-ynyl)phenyl)-4-oxo-2-(2-phthalimidoethyl)butyric acid 4-(4-(3-phenoxyprop-1-ynyl)phenyl)-4-oxo-2-(2-phthalimidoethyl)butyric acid 4-(4-heptyloxyphenyl)-4-oxo-2-(2-phthalimidoethyl)butyric acid 4-(4-hexyloxyphenyl)-4-oxo-2-(2-phthalimidoethyl)butyric acid 4-(4-decyloxyphenyl)-4-oxo-2-(2-phthalimidoethyl)butyric acid 4-(4-(2-benzyloxyethoxy)phenyl)-4-oxo-2-(2-phthalimidoethyl)butyric acid General Preparative Methods The compounds of the invention may be prepared readily by use of known chemical reactions and procedures. Nevertheless, the following general preparative methods are presented to aid the reader in synthesizing the inhibitors, with more detailed particular examples being presented below in the experimental section describing the working examples.

All variable groups of these methods are as described in the generic description if they are not specifically defined below. The variable subscript n is independently defined for each method. When a variable group with a given symbol (i.e. $R^9$) is used more than once in a given structure, it is to be understood that each of these groups may be independently varied within the range of definitions for that symbol.

General Method A

The compounds of formula (I) in which the $R^1$ group is alkyl, alkoxy, alkylthio, or polyether are conveniently prepared via a reaction sequence as shown in Method A. Thus, commercially available or readily prepared substituted benzenes II are reacted under Friedel-Crafts conditions with haloacetyl halide to yield intermediate III (for appropriate solvents and catalysts see E. Berliner, *Org. React.*, 5, 229 (1949) or H. Heaney, *Comp. Org. Synth.*, 2, 733 (1991)). Alternatively, II may first be reacted with acetyl halide to form IV, which in turn is halogenated with, for example, bromine to yield the intermediate of structure III. Some compounds of structure III, such as 2-bromo-4'-tetradecyloxyacetophenone (III in which $R^1=C_{14}H_{29}$ and X=Br), are commercially available.

Dialkyl malonate V ($R^9$=ethyl, methyl, allyl, 2-(trimethylsilyl)ethyl or t-butyl) is mono-alkylated with a substituted alkyl halide of structure VI to yield an intermediate of structure VII, which is then alkylated with III to form compound VIII (method A-1). Alternatively, the reaction sequence can be changed to first mono-alkylate V with III and then alkylate with VI to yield VIII (method A-2).

Malonate diester VIII is then converted to diacid IX, which is then heated to yield invention compound I-A. The conversion of VIII to IX can be achieved in a number of ways, depending on the sensitivity of functional groups contained in $R^1$ and $R^5$ to base or strong acid treatment. When $R^5$, for example, contains a base sensitive phthalimide group, $R^9$ is conveniently allyl and is removed by treatment with trans-dichlorobistriphenylphosphine palladate/pyrrolidine. Alternatively, $R^9$ can be tert-butyl, which is removed by treatment with HCl in a solvent such as dioxane at reflux, forming invention compound I-A directly. When the intermediate VIII contains no base sensitive groups, such as when $R^5$ is phenyl, $R^9$ may be removed by treatment with aqueous sodium or potassium hydroxide followed by acid work up to yield IX.

In the case that ether or thioether starting materials II or IV are not commercially available, they are prepared by reacting phenol, thiophenol or 4'-hydroxyacetophenone (IV in which $R^1$ is OH) with alkyl or aryl or arylalkyl halides in the presence of $K_2CO_3$ in a solvent such as THF or DMF. Alternatively, phenol, or 4'-hydroxyacetophenone may be reacted with alcohols using Mitsunobu conditions in procedures well known to those skilled in the art (see O. Mitsunobu, Synthesis, 1 (1981)).

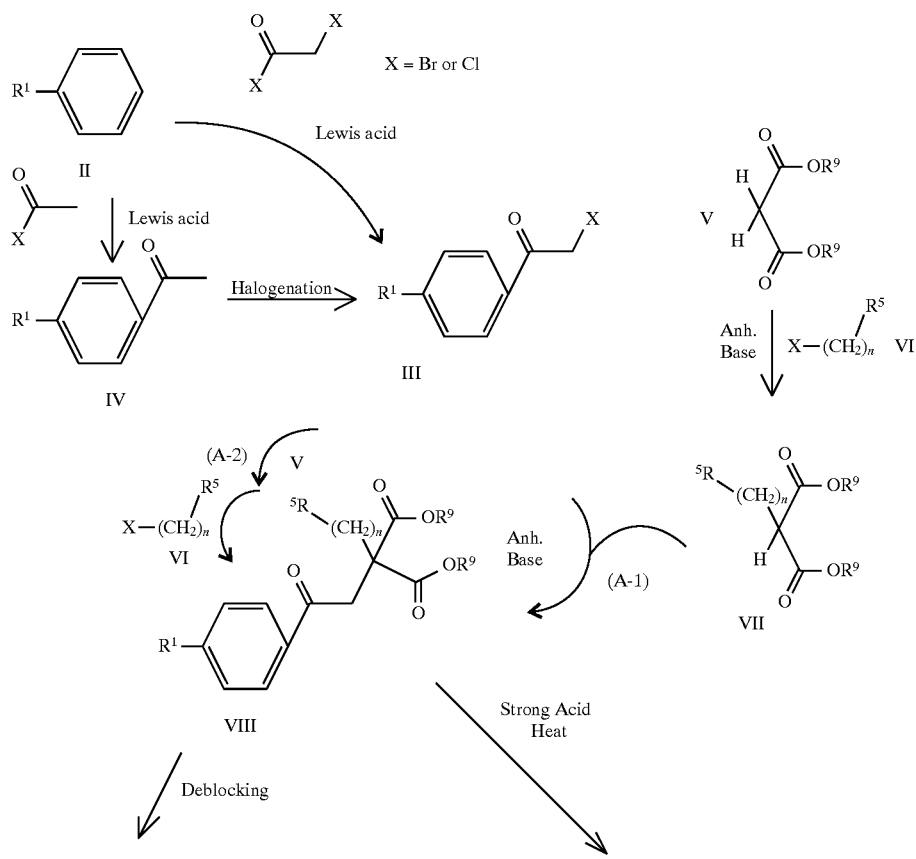

Method A

-continued
Method A

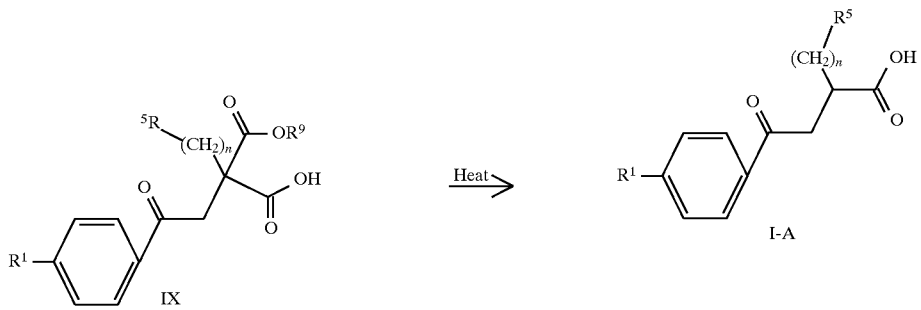

General Method B

The compounds of this invention in which $R^1$ is an alkynyl or substituted alkynyl are prepared according to general method B. Intermediate X is prepared according to method A by starting with commercial III ($R^1$=Br). Reaction of X with substituted acetylene XI in the presence of Cu(I)/palladate reagent gives invention compound I-B-1. If desired, these materials can be hydrogenated under standard conditions to yield invention compounds I-B-2 in which $R^1$ of formula I is substituted alkyl. In certain cases, $R^3$ may be an alcohol blocked as trialkylsilyl. In such cases the silyl group can be removed by treatment with acids such as trifluoroacetic acid or HF—pyridine reagent.

Method B

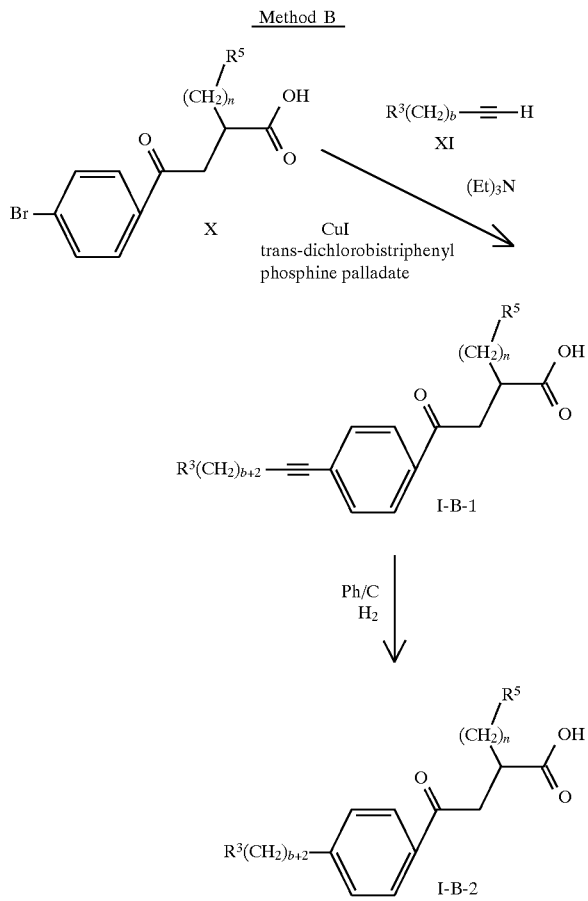

General Method C

In certain cases such as when $R^5$ is (3H)-benzo-1,2,3-triazin-4-on-3-yl, N-saccharinyl, (2H)-phthalazin-1-on-2-yl, 2-benzoxazolin-2-on-3-yl, 5,5-dimethyloxazolidine-2,4-dion-3-yl, or thiazolidine-2,4-dion-3-yl, the intermediates VI are not commercially available, but are prepared according to method C. The commercial heterocyclic compounds XII are reacted under Mitsunobu conditions with bromoalkanol XIII to yield the desired intermediates VI-C.

Method C

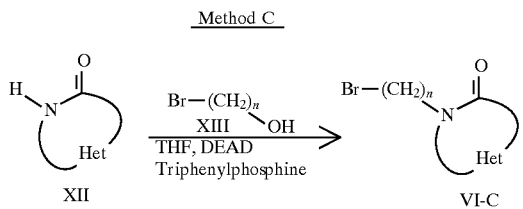

General Method D

The compounds of formula (I') which contain a substituted 5-member ring are most conveniently prepared by method D. In this method acid XIV (R=H) is prepared using the protocols described in Tetrahedron, Vol. 37, Suppl., 411 (1981). The acid is protected as an ester (R=benzyl or 2-(trimethylsilyl)ethyl) by use of coupling agents such as 1-(3-dimethylaminopropyl)-3-ethylcarbodiimide hydrochloride and procedures well known to those skilled in the art. Substituted bromophenyl XV is converted to its Grignard reagent by treatment with magnesium, then this is reacted with XIV to yield alcohol XVI. Alcohol XVI is eliminated via base treatment of its mesylate by using conditions well known to those skilled in the art to yield olefin XVII. Alternatively XV is converted to a trimethyltin intermediate via initial metallation of the bromide with n-butyllithium at low temperature (typically –78°) followed by treatment with chlorotrimethyltin, and XIV is converted to an enoltriflate by reaction with 2-[N,N-bis(trifluoromethylsulfonyl)amino]-5-chloropyridine in the presence of a strong aprotic base. The tin and enoltriflate intermediates are then coupled in the presence of a $Pd^o$ catalyst, CuI and $AsPh_3$ to yield directly intermediate XVII. Ozonolysis of XVII (workup with methylsufide) yields aldehyde XVIII. Alternatively treatment with $OsO_4$ followed by $HIO_4$ converts XVII to XVIII.

Conversion of key intermediate XVIII to compound I-D of formula (I') is accomplished in several ways, depending on the identity of side chain function $R^5$. Reaction of XVIII with Wittig reagents followed by hydrogenation yields products in which $R^5$ is arylalkyl. Reduction of aldehyde XVIII with LAH yields alcohol I-D ($R^5$=OH). The alcohol is converted to phenyl ethers or N-heterocyclic derivatives by use of the appropriate heterocycles and Mitsunobu conditions as shown in method C and well known to those skilled in the art; see O. Mitsunobu, Synthesis, 1 (1981). Alternatively, the alcohol of I-D ($R^5$=OH) is converted to a leaving group such as tosylate ($R^5$=OTs) or bromide ($R^5$=Br) by conditions well known to those skilled in the art and then the leaving group is displaced by sulfur or azide nucleophiles to yield products with $R^5$=thioether or azide which in turn is reduced and acylated to yield amides ($R^5$=NHAcyl). Direct acylation of the alcohol I-D ($R^5$=OH) yields compounds in which $R^5$=OAcyl and reaction of the alcohol with various alkyl halides in the presence of base yields alkyl ethers ($R^5$=$OR^2$). In each case a final step is removal of acid blocking group R to yield acids (R=H) by using conditions which depend on the stability of R and $R^5$, but in all cases well known to those skilled in the art such as removal of benzyl by base hydrolysis or of 2-(trimethylsilyl)ethyl by treatment with tetrabutylammonium fluoride.

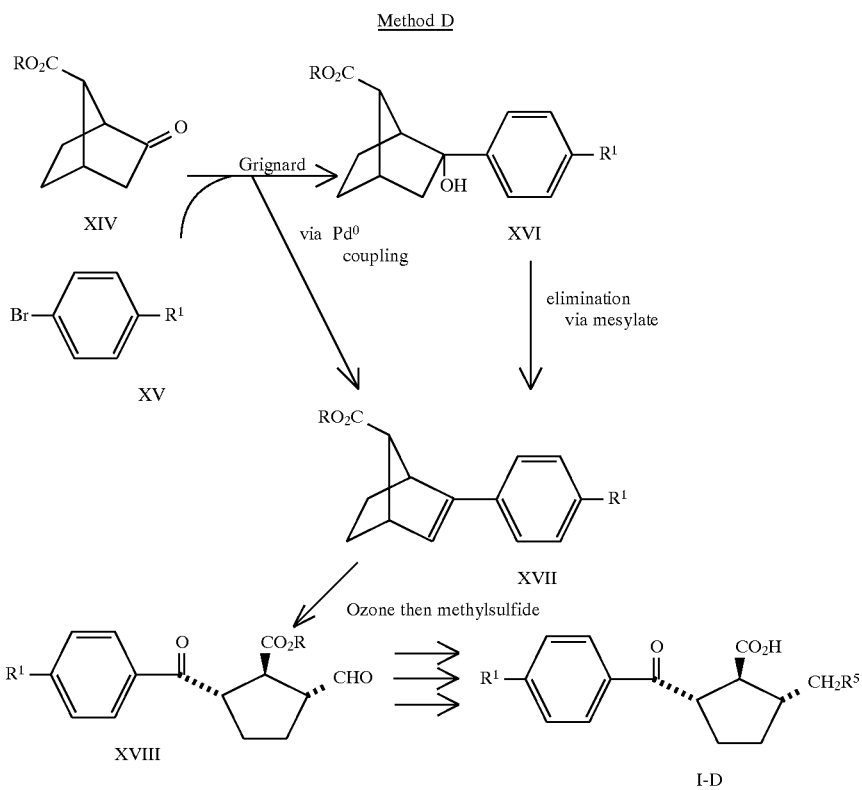

Method D

General Method E

Compounds of formula (I') containing four-membered rings are prepared according to general method E. The substituted four member ring starting material anhydride XXI is formed in a photochemical 2+2 reaction as shown between maleic anhydride XIX and allyl acetate XX. After a subsequent Friedel-Crafts reaction yielding XXII, the acetate can be removed by basic hydrolysis and the carboxyl protected, such as by conversion to 2-(trimethylsilyl)ethyl ester. The resultant intermediate XXIII can be converted to compounds of formula (I') with other $R^5$ groups by using procedures described in General Method D.

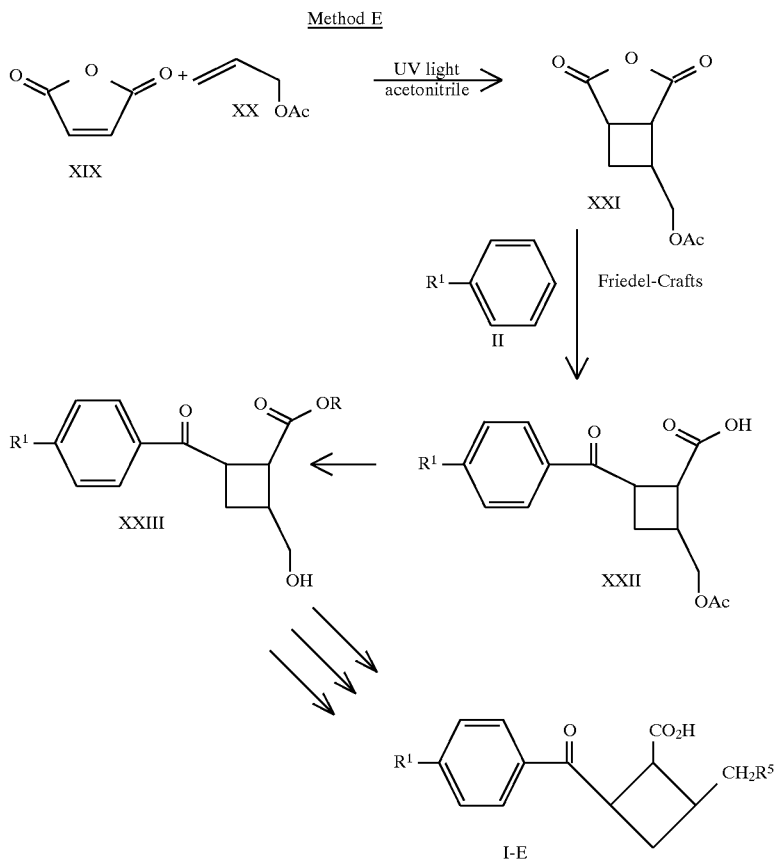

Suitable pharmaceutically acceptable salts of the compounds of the present invention include addition salts formed with organic or inorganic bases. The salt forming ion derived from such bases can be metal ions, e.g., aluminum, alkali metal ions, such as sodium of potassium, alkaline earth metal ions such as calcium or magnesium, or an amine salt ion, of which a number are known for this purpose. Examples include ammonium salts, arylalkylamines such as dibenzylamine and N,N-dibenzylethylenediamine, lower alkylamines such as methylamine, t-butylamine, procaine, lower alkylpiperidines such as N-ethylpiperidine, cycloalkylamines such as cyclohexylamine or dicyclohexylamine, 1-adamantylamine, benzathine, or salts derived from amino acids like arginine, lysine or the like. The physiologically acceptable salts such as the sodium or potassium salts and the amino acid salts can be used medicinally as described below and are preferred.

These and other salts which are not necessarily physiologically acceptable are useful in isolating or purifying a product acceptable for the purposes described below. For example, the use of commercially available enantiomerically pure amines such as (+)-cinchonine in suitable solvents can yield salt crystals of a single enantiomer of the invention compounds, leaving the opposite enantiomer in solution in a process often referred to as "classical resolution." As one enantiomer of a given invention compound is usually substantially greater in physiological effect than its antipode, this active isomer can thus be found purified in either the crystals or the liquid phase. The salts are produced by reacting the acid form of the compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

The compounds of the present invention have been found to inhibit the matrix metalloproteases MMP-3, MMP-9, and MMP-2, and are therefore useful for treating or preventing the conditions referred to above. As other MMPs not listed above share a high degree of homology with those listed above, especially in the catalytic site, it is deemed that compounds of the invention should also inhibit such other MMPs to varying degrees. Varying the substituents on the aryl portions of the molecules, as well as those of the butanoic acid chain of the claimed compounds, has been demonstrated to affect the relative inhibition of the listed MMPs. Thus compounds of this general class can be "tuned" by selecting specific substituents such that inhibition of specific MMP(s) associated with specific pathological conditions can be enhanced while leaving non-involved MMPs less affected.

The inhibitors of the present invention are contemplated for use in human and veterinary applications. Accordingly, this invention relates to a method for treating mammalian subjects (including humans and/or animals raised in the dairy, meat, sport, or fur industries or as pets, for example, mice, rats, horses, cattle, sheep, dogs, cats, etc.) suffering from matrix metalloprotease-mediated conditions such as those previously described, by administering an effective amount of a compound of the invention. In this treatment method the mammal is preferably a human. The effects which can be achieved are: alleviation of osteoarthritis, rheumatoid arthritis, septic arthritis, periodontal disease, corneal ulceration, proteinuria, aneurysmal aortic disease, dystrophobic epidermolysis bullosa, conditions leading to inflammatory responses, osteopenias mediated by MMP activity, tempero mandibular joint disease, or demyelating diseases of the nervous system; retardation of tumor metastasis or degenerative cartilage loss following traumatic joint injury; reduction of coronary thrombosis from atherosclerotic plaque rupture; or improved birth control. In this treatment method the amount of the inhibitor compound is effective to inhibit the activity of at least one matrix metalloprotease, resulting in achievement of the desired effect.

The compounds of the invention are employed in pharmaceutical compositions containing active ingredient(s) plus one or more pharmaceutically acceptable carriers, diluents, fillers, binders, and other excipients, depending on the administration mode and dosage form contemplated.

Administration of the inhibitors may be by any suitable mode known to those skilled in the art. Examples of suitable parenteral administration include intravenous, intraarticular, subcutaneous and intramuscular routes. Intravenous administration can be used to obtain acute regulation of peak plasma concentrations of the drug. Improved half-life and targeting of the drug to the joint cavities may be aided by entrapment of the drug in liposomes. It may be possible to improve the selectivity of liposomal targeting to the joint cavities by incorporation of ligands into the outside of the liposomes that bind to synovial-specific macromolecules. Alternatively intramuscular, intraarticular or subcutaneous depot injection with or without encapsulation of the drug into degradable microspheres e.g., comprising poly(DL-lactide-co-glycolide) may be used to obtain prolonged sustained drug release. For improved convenience of the dosage form it may be possible to use an i.p. implanted reservoir and septum such as the Percuseal system available from Pharmacia. Improved convenience and patient compliance may also be achieved by the use of either injector pens (e.g. the Novo Pin or Q-pen) or needle-free jet injectors (e.g. from Bioject, Mediject or Becton Dickinson). Prolonged zero-order or other precisely controlled release such as pulsatile release can also be achieved as needed using implantable pumps with delivery of the drug through a cannula into the synovial spaces. Examples include the subcutaneously implanted osmotic pumps available from ALZA, such as the ALZET osmotic pump.

Nasal delivery may be achieved by incorporation of the drug into bioadhesive particulate carriers (<200 $\mu$m) such as those comprising cellulose, polyacrylate or polycarbophil, in conjunction with suitable absorption enhancers such as phospholipids or acylcarnitines. Available systems include those developed by DanBiosys and Scios Nova.

Oral delivery may be achieved by incorporation of the drug into tablets, coated tablets, dragées, hard and soft gelatin capsules, solutions, emulsions or suspensions. Oral delivery may also be achieved by incorporation of the drug into enteric coated capsules designed to release the drug into the colon where digestive protease activity is low. Examples include the OROS-CT/Osmet™ and PULSINCAP™ systems from ALZA and Scherer Drug Delivery Systems respectively. Other systems use azo-crosslinked polymers that are degraded by colon specific bacterial azoreductases, or pH sensitive polyacrylate polymers that are activated by the rise in pH at the colon. The above systems may be used in conjunction with a wide range of available absorption enhancers.

Rectal delivery may be achieved by incorporation of the drug into suppositories.

The compounds of this invention can be manufactured into the above listed formulations by the addition of various therapeutically inert, inorganic or organic carriers well known to those skilled in the art. Examples of these include, but are not limited to, lactose, corn starch or derivatives thereof, talc, vegetable oils, waxes, fats, polyols such as polyethylene glycol, water, saccharose, alcohols, glycerin and the like. Various preservatives, emulsifiers, dispersants, flavorants, wetting agents, antioxidants, sweeteners, colorants, stabilizers, salts, buffers and the like are also added, as required to assist in the stabilization of the formulation or to assist in increasing bioavailability of the active ingredient(s) or to yield a formulation of acceptable flavor or odor in the case of oral dosing.

The amount of the pharmaceutical composition to be employed will depend on the recipient and the condition being treated. The requisite amount may be determined without undue experimentation by protocols known to those skilled in the art. Alternatively, the requisite amount may be calculated, based on a determination of the amount of target enzyme which must be inhibited in order to treat the condition. Typically, dosage levels from about 0.05 mg to about 150 mg per kilogram of body weight per day (about 4 mg to about 12 grams per adult human subject per day) are useful in the treatment of the above-indicated conditions. It is to be understood, however, that the specific dose level for any particular subject will depend upon a variety of factors including the subject's age, body weight, general health, sex, and diet, the activity and expected level of side effects of the specific compound employed, the time and route of administration, the rate of excretion, as well as drug combinations and the severity of the particular condition being treated.

The matrix metalloprotease inhibitors of the invention are useful not only for treatment of the physiological conditions discussed above, but are also useful in such activities as purification of metalloproteases, and in testing for matrix metalloprotease activity. Such activity testing can be both in vitro using natural or synthetic enzyme preparations or in vivo using, for example, animal models in which abnormal destructive enzyme levels are found spontaneously (use of genetically mutated or transgenic animals) or are induced by administration of exogenous agents or by surgery which disrupts joint stability.

Experimental

General Procedures

All reactions were performed in flame-dried or oven-dried glassware under a positive pressure of argon and were stirred magnetically unless otherwise indicated. Sensitive liquids and solutions were transferred via syringe or cannula and were introduced into reaction vessels through rubber septa. Reaction product solutions were concentrated using a Buchi evaporator unless otherwise indicated.

Materials

Commercial grade reagents and solvents were used without further purification except that diethyl ether and tetrahydrofuran were usually distilled under argon from benzophenone ketyl, and methylene chloride was distilled under argon from calcium hydride. Many of the specialty organic or organometallic starting materials and reagents were obtained from Aldrich, 1001 West Saint Paul Avenue, Milwaukee, Wis. 53233. Solvents are often obtained from EM Science as distributed by VWR Scientific.

Chromatography

Analytical thin-layer chromatography (TLC) was performed on Whatman® pre-coated glass-backed silica gel 60 A F-254 250 $\mu$m plates. Visualization of spots was effected by one of the following techniques: (a) ultraviolet illumination, (b) exposure to iodine vapor, (c) immersion of the plate in a 10% solution of phosphomolybdic acid in ethanol followed by heating, and (d) immersion of the plate in a 3% solution of p-anisaldehyde in ethanol containing 0.5% concentrated sulfuric acid followed by heating.

Column chromatography was performed using 230–400 mesh EM Science® silica gel.

Analytical high performance liquid chromatography (HPLC) was performed at 1 mL min$^{-1}$ on a 4.6×250 mm Microsorb® column monitored at 288 nm, and semi-preparative HPLC was performed at 24 mL min$^{-1}$ on a 21.4×250 mm Microsorb® column monitored at 288 nm.

Instrumentation

Melting points (mp) were determined with a Thomas-Hoover melting point apparatus and are uncorrected.

Proton ($^1$H) nuclear magnetic resonance (NMR) spectra were measured with a General Electric GN-OMEGA 300 (300 MHz) spectrometer, and carbon thirteen ($^{13}$C) NMR spectra were measured with a General Electric GN-OMEGA 300 (75 MHz) spectrometer. Most of the compounds synthesized in the experiments below were analyzed by nmr, and the spectra were consistent with the proposed structures in each case.

Mass spectral (MS) data were obtained on a Kratos Concept 1-H spectrometer by liquid-cesium secondary ion (LCIMS), an updated version of fast atom bombardment (FAB). Most of the compounds synthesized in the experiments below were analyzed by mass spectroscopy, and the spectra were consistent with the proposed structures in each case.

General Comments

For multi-step procedures, sequential steps are indicated by numbers. Variations within steps are indicated by letters. Dashed lines in tabular data indicates point of attachment.

EXPERIMENTAL PROCEDURES

Compound A

Preparation of 4-(4-bromophenyl)-4-oxo-2-(3-phenylpropyl) butyric acid

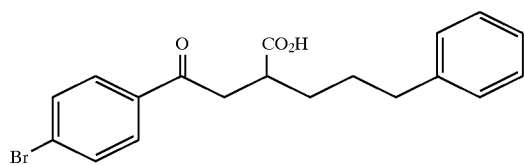

Step 1
Preparation of diethyl (3-phenylpropyl)malonate

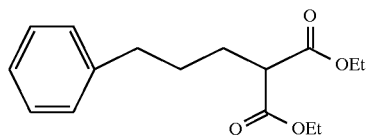

A dry 2-L, three-necked, round-bottomed flask was equipped with a stir bar, a pressure equalizing addition funnel, an argon inlet and a thermometer. The flask was charged with a suspension of sodium hydride (8.4 g of 95% NaH; ~0.33 mol) in dry THF (700 mL) and was cooled with an ice water bath. Diethyl malonate (48.54 g, 0.30 mol) was added dropwise from the addition funnel over 25 min. Stirring was continued for 1.5 h before adding 1-bromo-3-phenylpropane (47 mL, ~61 g, ~0.30 mol) over 10 min via the addition funnel. Rinses of the addition funnel (THF, 2×10 mL) were added to the reaction mixture and stirring was continued for 30 min. The addition funnel and thermometer were replaced with a reflux condenser and stopper, and the reaction was heated at reflux for 19 h. The mixture was cooled to room temperature and then with an ice water bath. Distilled water (400 mL) was slowly added with stirring. The layers were separated and the aqueous phase was extracted with chloroform (100 mL). The combined organics were washed with 10% HCl (250 mL) and the separated aqueous phase was back-extracted with chloroform (100 mL). The combined organics were washed with saturated NaHCO$_3$ (250 mL) and the separated aqueous phase was back-extracted with chloroform (100 mL). The organics were dried (Na$_2$SO$_4$) and concentrated to yield a yellow oil which was purified by distillation through a Vigreux column at reduced pressure (0.4 torr). The fraction boiling at 124°–138° C. was clean desired compound (57.21 g, 0.206 mol; 68% yield). TLC (hexanes-dichloromethane, 1:1): R$_f$=0.32.

Step 2
Preparation of diethyl 2-(3-phenylpropyl)-2-(2-oxo-2-(4-bromophenyl)-ethyl)malonate

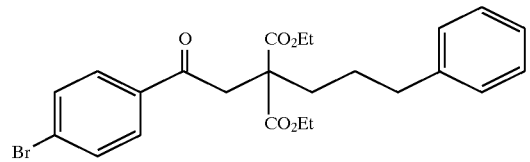

A one-necked, 1000-mL, round-bottomed flask equipped with a rubber septum and an argon needle inlet was charged with THF (300 mL) and diethyl (3-phenylpropyl)malonate (75.0 g, 270 mmol). To this solution was added sodium hydride (6.48 g, 270 mmol) slowly in portions at 0° C. The resulting mixture was stirred for 30 min at 0° C. and 1 h at room temperature. The reaction mixture was then cooled to 0° C. and 2,4'-dibromoacetophenone (90.3 g, 325 mmol) was added. The resulting mixture was stirred for 30 hours at room temperature. The reaction mixture was diluted with brine (300 mL) and extracted with EtOAc (200 ml, 150 mL×3). The combined organic phases were dried over MgSO$_4$, filtered, and concentrated to provide a brown oil which was used directly in step 3. TLC (5% ethyl acetate-hexanes) R$_f$=0.24.

Step 3
Preparation of 2-(3-phenylpropyl)-2-(2-oxo-2-(4-bromophenyl)ethyl)malonic acid

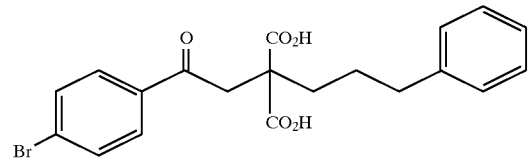

A one-necked, 1000-mL, round-bottomed flask equipped with an argon inlet adapter was charged with ethanol (150 mL), THF (150 mL), the product of step 2, and an aqueous 2 N sodium hydroxide solution (300 mL). The resulting mixture was stirred for 48 h at room temperature after which a TLC assay indicated the reaction was not completed. More NaOH (166 g of 50% aqueous solution) was added and the reaction mixture was stirred at room temperature for 24 hours. The reaction mixture was then acidified with a 50% HCl solution to pH 1, and extracted with EtOAc (200 ml and 150 ml×3). The combined organic phases were dried over MgSO$_4$, filtered, and concentrated to provide 150 g of a yellow solid which was used directly in step 4.

Step 4

The product of step 3 above was dissolved in 200 ml of dioxane and stirred at 85°–90° C. for 12 hours and then at reflux. for 24 hours. The reaction mixture was then concentrated in vacuo and the resultant residue was recrystallized from EtOAc/hexanes to give 53 g (43%) of 4-(4-bromophenyl)-4-oxo-2-(3-phenylpropyl)butyric acid (Compound A) as a yellow solid. MP 147° C.

Compound B

Preparation of 4-(4-bromophenyl)-4-oxo-2-(2-phthalimidoethyl) butyric acid

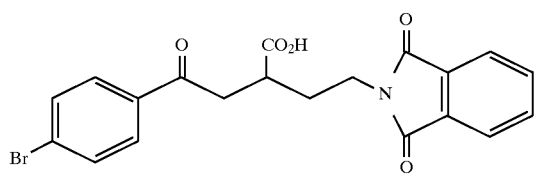

Step 1
Preparation of diallyl malonate

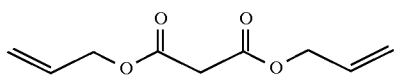

A solution of malonic acid (100 g, 0.96 mol) in allyl alcohol (250 mL) was treated with sulfuric acid (0.25 mL) and heated to 70° C. for 12 h. After cooling to room temperature, the solution was concentrated to about ⅓ of its original volume and diluted with hexanes (500 mL). The mixture was washed successively with satd. aq. $K_2CO_3$ and NaCl. The organic layer was dried over $Na_2SO_4$, filtered and concentrated under reduced pressure. Purification by distillation (85° C. @ 0.01 mmHg) provided diallyl malonate (156 g, 88%) as a colorless oil. $^1$H NMR (300 MHz, CDCl$_3$) d 5.85 (m, 2H), 5.30 (m, 2H), 5.20 (m, 2H), 4.60 (m, 4H), 3.40 (s, 2H).

Step 2
Preparation of diallyl (2-phthalimidoethyl)malonate

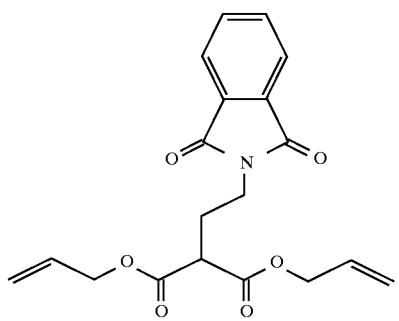

A solution of sodium hydride (4.35 g, 0.18 mol) in freshly distilled THF (100 mL) was cooled to 0° C. and treated with diallyl malonate (35 g, 0.19 mol) over 40 min via a dropping funnel. After stirring at room temperature for 30 min, N-(2-bromoethyl)phthalimide (43.9 g, 0.17 mol) was added to the solution in one portion and the mixture was heated to reflux. After 48 h the solution was cooled to 0° C., quenched with 2N HCl and concentrated to about 20% of its original volume. The concentrate was diluted with ethyl acetate (300 mL) and washed successively with satd. aq. $K_2CO_3$ and NaCl. The organic layer was dried over MgSO$_4$, filtered and concentrated under reduced pressure. Purification by flash column chromatography (5–25% ethyl acetate:hexanes) provided diallyl (2-phthalimidoethyl)malonate (41.2 g, 67%) as a colorless oil. $^1$H NMR (300 MHz, CDCl$_3$) d 7.82 (m, 2H), 7.72 (m, 2H), 5.85 (m, 2H), 5.30 (m, 2H), 5.22 (m, 2H), 4.60 (m, 4H), 3.80 (t, J=6.6 Hz, 2H), 3.46 (t, J=7.2 Hz, 1H), 2.30 (dd, J=13.8, 6.9 Hz, 2H).

Step 3
Preparation of diallyl 2-(2-phthalimidoethyl)-2-(2-oxo-2-(4-bromo-phenyl)ethyl)malonate

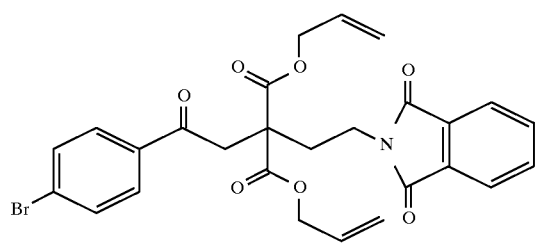

The general procedure of step 2 for the preparation of Compound A was used to prepare the above substituted diallyl malonate intermediate using diallyl (2-phthalimidoethyl)malonate instead of diethyl (3-phenylpropyl)malonate and sodium t-butoxide instead of sodium hydride.

Step 4
Preparation of 2-(2-phthalimidoethyl)-2-(2-oxo-2-(4-bromophenyl)-ethyl)malonic acid

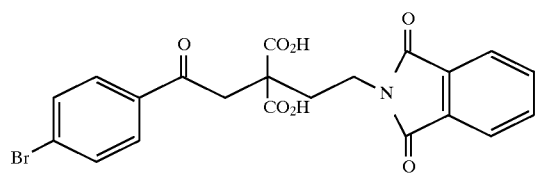

A one-necked, 100-mL, round-bottomed flask equipped with an argon inlet adapter was charged with dioxane (50 mL), the crude product of step 3 (26 mmol assuming 100% yield for step 3) and pyrrolidine (4.8 mL, 57 mmol, 2.2 eq.). The mixture was degassed by subjecting to slight vacuum and flushed with argon. Then trans-dichlorobistriphenylphosphine palladate (325 mg, 0.26 mmol) was added. The resulting mixture was stirred for 5 days at room temperature and concentrated. The residue was used in step 5 directly.

Step 5

The general method step 4 for the preparation of Compound A was used to prepare 4-(4-bromophenyl)-4-oxo-2-(2-phthalimidoethyl) butyric acid (Compound B) from the product of step 4 above. MP 185° C. (decomposition).

Compound C

Preparation of 4-phenyl-4-oxo-2-(3-phenylpropyl)butyric acid

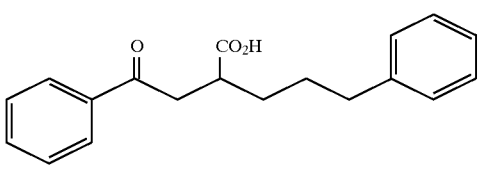

A one-necked, 25 mL, round-bottomed flask equipped with a rubber septum, stirring bar and a reflux condenser was charged with Compound A (0.750 g. 2.0 mmol) and tribenzyl amine (1.334 g, 4.8 mmol). The system was vacuum dried and flushed with argon. Then tetrakistriphenylphosphine palladium(0) (0.124 g, 0.10 mmol) was added and the system was vacuum dried and flushed with argon again. $CH_3CN$ (5 mL) and DMSO (5 mL) were added and the mixture was stirred at room temperature for 15 minutes. To the resulting clear yellow solution was added poly (methylhydrosiloxane) (0.8 mL) and the mixture was stirred at 105° C. for 16 hours. The reaction mixture was then cooled to room temperature, diluted with EtOAc (200 mL) and washed with 1N HCl (50 mL×3). The organic layer was separated, dried over $MgSO_4$ and concentrated to give 1.5 g of the crude product, which was purified via column chromatography on 50 g of silica gel (15%, 30% and 45% ethyl acetate in hexanes with 0.5% HOAc, 500 mL each) and subsequently recrystallized from $CH_2Cl_2$/hexane to afford 0.181 g (31%) of Compound C. MP 84°–85° C.; MS HRMS 297.14907 (M+H)$^+$, calc 296.1407.

Compound D

Preparation of 4-phenyl-4-oxo-2-(2-phthalimidoethyl) butyric acid

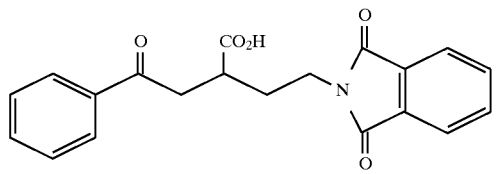

The general procedure used for the preparation of Compound C was used to prepare Compound D from Compound B. MP 165°–166° C.; MS HRMS 352.11850 (M+H)$^+$, calc 351.1102.

Example 1

Preparation of 4-(4-(3-hydroxyprop-1-ynyl)phenyl)-4-oxo-2-(3-phenylpropyl)butyric acid
Structure shown in Table 1

A one-necked, 25-mL, round-bottomed flask equipped with an argon inlet adapter was charged with Compound A (750 mg, 2 mmol), CuI (19 mg, 0.10 mmol) and trans-dichlorobistriphenylphosphine palladate (70 mg, 0.056 mmol). The resulting mixture was vacuum dried and flushed with argon. DMF (5 mL), $Et_3N$ (5 mL) and propargyl alcohol (3 mL) were added and the resulting mixture was stirred at 95° C. for 3 days The reaction mixture was then diluted with EtOAc (100 mL), filtered through celite and concentrated in vacuo. The residue was purified on silica gel twice (using 5% i-PrOH in $CH_2Cl_2$ for the first column and 25% EtOAc in hexanes with 0.5% HOAc for the second column) to furnish 108 mg of the desired product as an oil. MS (FAB-LSIMS) 352 [M+1]$^+$.

Examples 2 and 3

Preparation of 4-(4-(hex-1-ynyl)phenyl)-4-oxo-2-(3-phenylpropyl)butyric acid and 4-(4-(6-hydroxyhex-12-ynyl)phenyl)-4-oxo-2-(3-phenylpropyl)butyric acid
Structures shown in Table 1

The general procedure of Example 1 was used to prepare the desired compounds, starting with the appropriate substituted acetylenes instead of propargyl alcohol.

TABLE 1

| Example | R | isomer | MP (°C.)/other characterization |
|---------|---|--------|-------------------------------|
| 1 | HOCH$_2$C≡C | R, S | liquid |
| 2 | CH$_3$(CH$_2$)$_3$C≡C | R, S | 89 |
| 3 | HO(CH$_2$)$_4$C≡C | R, S | 60 |

Compound E And Example 4

Preparation of 4-(6-(tert-butyldimethylsylyloxy)hex-1-ynyl)-4-oxo-2-(2-phthalimidoethyl)butyric acid and 4-(hex-1-ynyl)-4-oxo-2-(2-phthalimidoethyl)butyric acid
Structures shown in Table 2

The general procedure of Example 1 was used to prepare Compound E and the compound of Example 4, using the appropriate acetylenes in place of propargyl alcohol and Compound B in place of Compound A.

Example 5

Preparation of 4-(4-(6-hydroxyhex-1-ynyl)phenyl)-4-oxo-2-(2-phthalimidoethyl)butyric acid
Structure shown in Table 2

A one-necked, 25-mL, round-bottomed flask equipped with an argon inlet adapter was charged with a solution of Compound E (150 mg, 0.27 mmol) in $CH_2Cl_2$ (4 mL). Hydrogen fluoride—pyridine reagent (2 mL, Fluka) was added and the resulting mixture was stirred at 0° C. for 10 minutes and then room temperature for 25 minutes. The reaction mixture was then poured into aqueous NaHCO$_3$ (150 mL) and extracted with $CH_2Cl_2$ (100 mL). The organic layer was washed with 1N HCl twice, dried over $MgSO_4$ and concentrated to give 160 mg crude product which upon chromatographic purification furnished 100 mg of the desired product.

Example 6

Preparation of 4-(4-(3-hydroxyprop-1-ynyl)phenyl)-4-oxo-2-(2-phthalimidoethyl)butyric acid
Structure shown in Table 2

The general procedures for the preparation of Compound E and the compound of Example 5 were used in sequence by starting with 3-(t-butyldimethylsilyloxy)propyne rather than 6-(t-butyldimethylsilyloxy)-1-hexyne to prepare the desired product. MS HRMS 406.12906 (M+H), calc 405.1207.

Example 7

Preparation of 4-(4-hexylphenyl)-4-oxo-2-(2-phthalimidoethyl) butyric acid
Structure shown Table 2

A one-necked, 10-mL, round-bottomed flask equipped with a rubber septum and a hydrogen balloon connected via a needle inlet was charged with 2 mL of dioxane, the compound of Example 4 (0.200 g, 0.46 mmol) and 5% palladium on carbon (0.005 g). The resulting mixture was stirred for 24 h at room temperature and filtered through Celite. After removing the solvent in vacuo, the residue was recrystallized from EtOAc/hexane to give the desired product (130 mg, 65%).

Examples 8 and 9

Preparation of 4-(4-(dodec-1-ynyl)phenyl)-4-oxo-2-(2-phthalimidoethyl)butyric acid and 4-(4-(3-phenoxyprop-1-ynyl)phenyl)-4-oxo-2-(2-phthalimidoethyl)butyric acid Structures shown in Table 2

The general procedure for the preparation of the compound of Example 1 can be used to prepare the compounds of Examples 8 and 9 by using either 1-dodecyne or phenylpropargyl ether respectively in place of propargyl alcohol, and Compound B instead of Compound A.

TABLE 2

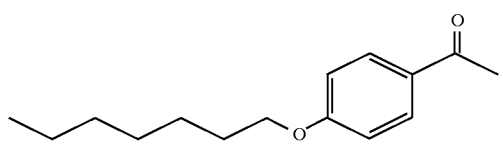

| Example | R | isomer | MP. (°C.)/other characterization |
|---|---|---|---|
| Comp. E | t-BuMe$_2$SiO(CH$_2$)$_4$C≡C | R, S | 151–152 |
| 4 | CH$_3$(CH$_2$)$_3$C≡C | R, S | 136 |
| 5 | HO(CH$_2$)$_4$C≡C | R, S | 131–132 |
| 6 | HOCH$_2$C≡C | R, S | NA |
| 7 | n-C$_6$H$_{13}$ | R, S | 109 |
| 8 | CH$_3$(CH$_2$)$_9$C≡C | R, S | |
| 9 | C$_6$H$_5$OCH$_2$C≡C | R, S | |

Example 10

Preparation of 4-(4-heptyloxyphenyl)4-oxo-2-(2-phthalimidoethyl) butyric acid

Structure shown in Table 3

Step 1

Preparation of 4'-heptyloxyacetophenone

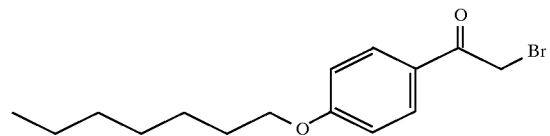

A 25 mL round bottom flask containing 4'-hydroxyacetophenone (Aldrich, 1.00 g, 7.35 mmol) and dry potassium carbonate (1.02 g, 7.35 mmol) was purged with argon and charged with anhydrous DMF (Aldrich, 7.5 mL) followed by 1-iodoheptane (Aldrich, 1.20 mL, 7.35 mmol). The mixture was stirred at room temperature for 47 h, then diluted with water and extracted with ethyl acetate (2×). The organic phases were combined and washed successively with saturated sodium bicarbonate and brine, dried over magnesium sulfate, filtered and concentrated to afford 1.7626 g of a beige oil. Flash chromatography (40 mL silica, 20% ethyl acetate-hexane) of the crude product afforded 1.5346 g (6.5487 mmol, 89%) of pure 4'-heptyloxyacetophenone as a colorless oil. R$_f$ 0.48 (25% ethyl acetate-hexane).

Step 2

Preparation of 4'-heptyloxy-2-bromoacetophenone

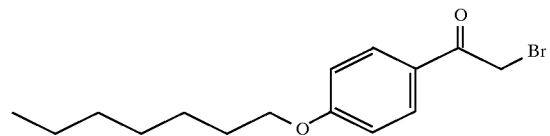

A 25 mL three neck round bottom flask fitted with a stir bar, addition funnel, septa, and argon inlet was purged with argon, then dried with a heat gun. The flask was charged with anhydrous THF (Aldrich, 5.58 mL), cooled to about –70° C., then lithium bis(trimethylsilyl)amide (Aldrich, 1.0M, 3.36 mL, 3.36 mmol) and chlorotrimethylsilane (Aldrich, 0.43 mL, 3.36 mmol) were added. A solution of 4'-heptyloxyacetophenone (from step 1) in dry THF (3.72 mL) under argon was added dropwise over 20 min, maintaining an internal temperature of about –70° C., and the solution was stirred for an additional 38 min at –78° C. N-Bromosuccinimide (Aldrich, 658 mg, 3.70 mmol) was added neat and in one portion, then stirred at –78° C. for another 40 minutes before the solution was partitioned between water and hexane. The organic layer was separated and washed twice with brine, dried over magnesium sulfate, filtered, and concentrated to afford 1.0740 g of a yellow oil. Flash chromatography (115 mL silica, 2% ethyl acetate-hexane) afforded 0.4533 g (1.447 mmol, 43%) of a white solid as the desired product. R$_f$ 0.52 (25% ethyl acetate-hexane).

Step 3

Preparation of diallyl 2-(2-phthalimidoethyl)-2-(2-oxo-2-(4-heptyloxy-phenyl)ethyl)malonate

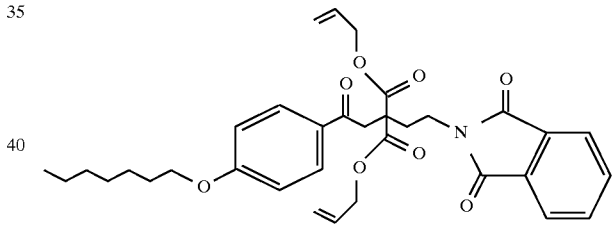

A solution of sodium tert-butoxide (Aldrich, 150 mg, 1.56 mmol) in dry THF (Aldrich, 1.0 mL) under argon was cooled in an ice bath. To this solution, a solution of diallyl (2-phthalimidoethyl)malonate (507 mg, 1.42 mmol) in dry THF (0.9 mL) was added. After about 20 min, a solution of 2-bromo-4'-heptyloxyacetophenone (from step 2, 444 mg, 1.42 mmol) in dry THF (1.4 mL) was added via syringe and stirred at room temperature for 1.5 h before sodium iodide (neat, 2.1 mg, 0.01 mmol) was added. The mixture was stirred for 89 h and then quenched with 10% HCl (8 mL), diluted with water, and extracted with ethyl acetate. The organic layer was washed with water and brine (2×), dried over magnesium sulfate, filtered, and concentrated to afford 721.3 mg of a yellow oil. Silica gel column chromatography (10% ethyl acetate-hexane) afforded 415.4 mg (0.704 mmol, 50%) of a colorless oil as the desired product. R$_f$ 0.22 (25% ethyl acetate-hexane).

Step 4

A 25 mL round bottom flask containing the product of step 3 (415.4 mg, 0.7044 mmol) under argon was charged with dioxane (14.6 mL) and degassed. To this solution, tetrakis(triphenylphosphine)palladium (Alfa, 11 mg, 10 μmol) was added, followed by pyrrolidine (Aldrich, 129 μL, 1.55 mmol) and the mixture was stirred at room temperature for 24 h before the milky white mixture was heated to reflux for two hours. The resulting beige solution was cooled to room temperature and concentrated to afford 375.6 mg of a beige oil. Flash column chromatography (silica, 1% methanol-dichloromethane) afforded 35.9 mg (0.077 mmol, 11%) of the title compound as a colorless oil, which solidified upon standing, from the cleanest fractions. MP 121°–122°; TLC (10% methanol-dichloromethane) $R_f$ 0.56.

Example 11
Preparation of 4-(4-hexyloxyphenyl)-4-oxo-2-(2-phthalimidoethyl) butyric acid
Structure shown in Table 3
Step 1
Preparation of phenyl hexyl ether

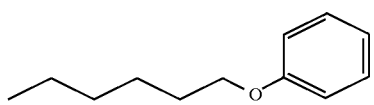

A solution of hexyl iodide (1.56 mL, 10.6 mmol) and phenol (1.0 g, 10.6 mmol) in dry THF (25 mL) over $K_2CO_3$ (1.46 g) was refluxed in a round bottom flask under argon overnight. The resulting reaction mixture was diluted with ethyl acetate and washed in sequence with saturated $Na_2CO_3$, 10% HCl, and brine. The extract was dried over $MgSO_4$ and evaporated in vacuo to yield 1.35 g of the desired product which was used directly in the next step without purification.

Step 2
Preparation of 4'-hexyloxy-2-bromoacetophenone

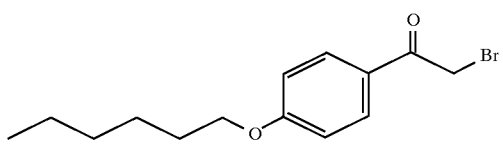

A solution of the product of step 1 (250 mg, 1.40 mmol) in methylene chloride (5 mL) was stirred at ambient temperature under argon as aluminum trichloride (205.5 mg, 1.5 mmol) and then bromoacetyl bromide (0.13 mL, 1.5 mmol) were added in sequence. The reaction mixture was stirred overnight at ambient temperature and then poured over ice/conc. HCl and extracted with methylene chloride. The extract was evaporated in vacuo. The reaction was repeated with 500 mg of the product of step 1 and proportional amounts of the other reagents, the only change being addition of $AlCl_3$ lastly at 0° C. and then stirring at 0° for 2h and finally at ambient temperature overnight before isolation of product as in the first run. The crude products from both runs were combined and chromatographed over silica gel using hexane and ethyl acetate mixtures to yield 233 mg of purified desired product.

Steps 3 and 4
The general procedures of steps 3 and 4 of Example 10 but using the product of step 2 above instead of 4'-heptyloxy-2-bromoacetophenone were used to prepare the compound of Example 11.

Example 12
Preparation of 4-(4-decyloxyphenyl)-4-oxo-2-(2-phthalimidoethyl) butyric acid
Structure shown in Table 3
The desired decyl compound was prepared in a similar manner as Example 10 except that iododecane was used instead of iodoheptane.

Example 13
Preparation of 4-(4-(2-benzyloxyethoxy)phenyl)-4-oxo-2-(2-phthalimidoethyl)butyric acid
Structure shown in Table 3
Step 1: Preparation of 4'-((2-benzyloxyethoxy)phenyl) acetophenone

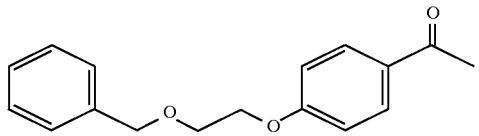

To a solution of triphenylphosphine (Aldrich, 11.56 g, 44.07 mmol) in 50 mL diethyl ether and 50 mL THF was added diethylazodicarboxylate (Aldrich, 6.94 mL, 44.07 mmol). The solution was stirred at room temperature for five min before 4'-hydroxyacetophenone (Aldrich, 5.00 g, 36.72 mmol) was added and after stirring for about 10 min, 2-benzyloxyethanol (Aldrich, 5.22 mL, 36.72 mmol) was added. After stirring for 4.75 h, the solution was concentrated, diluted with diethyl ether, washed with water (3×) and brine, dried over magnesium sulfate, filtered, and concentrated to afford 27.96 g of tan oil. This material was dissolved in ether, the precipitate was filtered, and the filtrate was concentrated to afford 25.71 g of beige oil. Column chromatography (silica, 2% methanol-dichloromethane) afforded 1.6767 g (6.20 mmol, 17%) of beige oil as the desired product. TLC (25% ethyl acetate-hexane) $R_f$ 0.24.

Steps 2–4
The desired material was produced using the general methods of steps 2 through 4 of Example 10 with the exception that the product of step 1 above was used instead of 4'-heptyloxyacetophenone.

Compound F
Preparation of 4-(4-tetradecyloxyphenyl)-4-oxo-2-(2-phthalimidoethyl)butyric acid
Structure shown in Table 3
The desired compound was prepared using the general methods of steps 3 and 4 of Example 10 with the exception that the commercially available intermediate 2-bromo-4'-tetradecyloxyacetophenone (Salor) was used instead of 2-bromo-4'-heptyloxyacetophenone.

Compound G
Preparation of 4-(4-methoxyphenyl)-4-oxo-2-(2-phthalimidoethyl)butyric acid
Structure shown in Table 3
Step 1
Preparation of dimethyl 2-(2-phthalimidoethyl)-2-(2-oxo-2-(4-methoxy-phenyl)ethyl)malonate

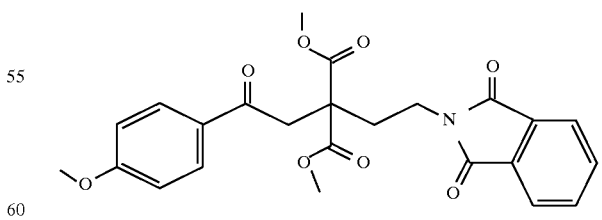

The desired compound was prepared using the general method of Example 10, step 3, with the exceptions that the commercially available intermediate 2-bromo-4'-methoxyacetophenone (Aldrich) was used instead of 2-bromo-4'-heptyloxyacetophenone, and the bis-dimethyl ester was used instead of the bis-diallyl ester.

Step 2

The bis-dimethyl ester of step 1 (94.4 mg) was placed in a 2 mL micro vial, dissolved in 20% HCl-HOAc, the vial was sealed and heated to about 105° C. After 15 h, the solution was cooled to room temperature, diluted with water, and partitioned with ethyl acetate. The organic layer was washed five times with water, the combined aqueous layers were back-extracted with ethyl acetate, the organic layers were combined, dried over magnesium sulfate, filtered, and concentrated to afford 73.3 mg of a black semi-solid. Crystallization from ethyl acetate-hexane afforded 28.1 mg as a brown solid. This material was then washed several times with ethyl acetate and the remaining solid was isolated as the desired product (10.8 mg of beige solid, 28.3 μmol, 14%). MP 191°–192° C.

TABLE 3

| Example | R | isomer | m.p. (°C.)/other characterization |
|---|---|---|---|
| 10 | n-C$_7$H$_{15}$O | R, S | 121–122 |
| 11 | n-C$_6$H$_{13}$O | R, S | |
| 12 | n-C$_{10}$H$_{21}$O | R, S | 119–120 |
| 13 | 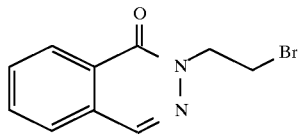 | R, S | 161–162 |
| Comp. F | n-C$_{14}$H$_{29}$O | R, S | 125–126 |
| Comp. G | CH$_3$O | R, S | 191–192 |

Example 14

Preparation of 4-(4-(dodecylthio)phenyl)-4-oxo-2-(2-((2H)-phthalazin-1-on-2-yl)ethyl)butyric acid

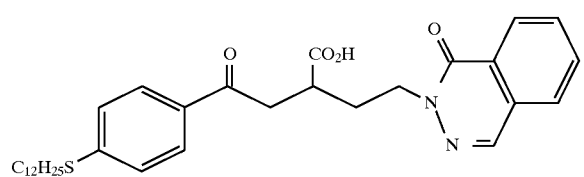

Step 1

Preparation of 2-(2-bromoethyl)phthalazin-1-one

A solution of phthalazinone (1.00 g, 6.84 mmol) and triphenyl phosphine (1.79 g, 6.84 mmol) in THF (25 mL) was cooled to 0° C. and treated with bromo ethanol (0.480 mL, 6.84 mmol) and diethylazodicarboxylate (1.07 mL, 6.84 mmol). After stirring 1 h at 0° C. the solution was warmed to room temperature and stirred for an additional 12 h. The resulting mixture was concentrated and purified by flash column chromatography (35% ethyl acetate-hexanes) to afforded 1.40 g (81%) of the desired compound as a white solid. TLC: R$_f$ 0.65 (40% ethyl acetate-hexane).

Step 2

Preparation of diallyl 2-(2-((2H)-phthalazin-1-on-2-yl)ethyl)malonate

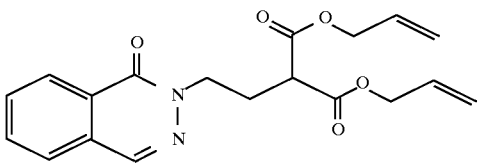

A solution of sodium hydride (0.040 g, 1.54 mmol) in THF (5 mL) was cooled to 0° C. and carefully treated with diallyl malonate (0.260 g, 1.41 mmol). After warming to room temperature and stirring for 20 min, bromo ethyl phthalazinone from step 1 (0.325 g, 1.28 mmol) was added in one portion and the mixture was heated to reflux for 18 h. The reaction mixture was diluted with saturated aq. NH$_4$Cl (20 ml) and EtOAc (20 ml). The resulting organic phase was washed with a water, dried over MgSO$_4$, filtered and concentrated to afford 0.240 g (52%) of a yellow oil. TLC: R$_f$ 0.60 (40% ethyl acetate-hexane).

Step 3

Preparation of 2-bromo-4'-dodecylthioacetophenone

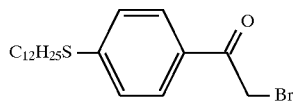

The general methods of steps 1 and 2 of Example 11 can be used to prepare the desired compound by using dodecyl iodide instead of hexyl iodide and thiophenol instead of phenol.

Steps 4 and 5

The general procedures of steps 3 and 4 of Example 10, but using the product of step 3 above instead of 4'-heptyloxy-2-bromoacetophenone and the product of step 2 above instead of diallyl (2-phthalimidoethyl)malonate, can be used to prepare the compound of Example 14.

Example 15

Preparation of 4-(4-pentyloxyphenyl)-4-oxo-2-(2-((3H)-benzo-1,2,3-triazin-4-on-3-yl)ethyl)butyric acid Structure in Table 4

Steps 1 and 2

Preparation of diallyl 2-(2-((3H)-benzo-1,2,3-triazin-4-on-3-yl)ethyl)malonate

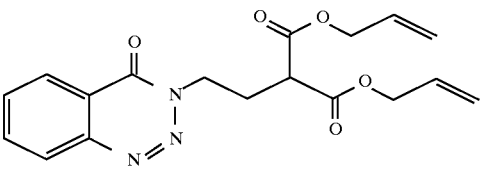

The general methods of steps 1 and 2 of Example 14 can be used to prepare the above benzotriazinone intermediate by starting with benzo-1,2,3-triazin-4(3H)-one in place of phthalazinone.

Step 3
Preparation of 2-bromo-4'-pentoxyacetophenone

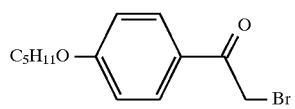

The general methods of steps 1 and 2 of Example 11 can be used to prepare 2-bromo-4'-pentoxyacetophenone by using pentyl iodide instead of hexyl iodide.

Steps 4 and 5

The general procedures of steps 3 and 4 of Example 10, but using the product of step 3 above instead of 4'-heptyloxy-2-bromoacetophenone and the product of step 2 above instead of diallyl (2-phthalimidoethyl)malonate, can be used to prepare the compound of Example 15.

Examples 16, 17, 18 and 19

Preparation of 4-(4-pentyloxyphenyl)-4-oxo-2-(2-(N-saccharinyl)ethyl)butyric acid; 4-(4-pentyloxyphenyl)-4-oxo-2-(2-(benzoxazolin-2-on-3-yl)ethyl)butyric acid; 4-(4-pentyloxyphenyl)-4-oxo-2-(2-(5,5-dimethyloxazolidine-2,4-dion-3-yl)ethyl)butyric acid: and 4-(4-pentyloxyphenyl)-4-oxo-2-(2-(thiazolidine-2,4-dion-3-yl)ethyl)butyric acid Structures shown in Table 4

The general procedures referred to in Example 15 can be used to prepare these compounds by using saccharine, 2-benzoxazolinone, 5,5-dimethyloxazolidine-2,4-dione, or thiazolidine-2,4-dione, respectively, instead of benzo-1,2,3-triazin-4(3H)-one.

TABLE 4

| Example | R⁵ | isomer | m.p. (°C.)/other characterization |
|---|---|---|---|
| 15 | (1,2,3-triazin-4(3H)-on-3-yl) | R, S | |
| 16 | (saccharinyl) | R, S | |
| 17 | (benzoxazolin-2-on-3-yl) | R, S | |
| 18 | (5,5-dimethyloxazolidine-2,4-dion-3-yl) | R, S | |
| 19 | (thiazolidine-2,4-dion-3-yl) | R, S | |

Biological Protocols and In Vitro Test Data
P218 Quenched Fluorescence Assay for MMP Inhibition The P218 quenched fluorescence assay (Microfluorometric Profiling Assay) is a modification of that originally described by C. G. Knight et al., FEBS Letters, 296, 263–266 (1992) for a related substrate and a variety of matrix metalloproteinases (MMPs) in cuvettes. The assay was run with each exemplary compound of the invention and the three MMPs, MMP-3, MMP-9 and MMP-2, analyzed in parallel, adapted as follows for a 96-well microtitre plate and a Hamilton AT® workstation.

P218 Fluorogenic Substrate

P218 is a synthetic substrate containing a 4-acetyl-7-methoxycoumarin (MCA) group in the N-terminal position and a 3-(2,4-dinitrophenyl)-(L)-2,3-diaminopropionyl (DPA) group internally. This is a modification of a peptide reported by Knight (1992) that was used as a substrate for matrix metalloproteinases. Once the P218 peptide is cleaved (putative clip site at the Ala-Leu bond), the fluorescence of the MCA group can be detected on a fluorometer with excitation at 328 nm and emission at 393 nm. P218 is currently being produced by BACHEM Bioscience, Inc. exclusively for the Bayer Corp. P218 has the structure:

Recombinant Human CHO Stromelysin (MMP-3)
Recombinant Human CHO Pro-MMP-3
Human CHO prostromelysin-257 (pro-MMP-3) was expressed and purified as described by T. J. Housley et al., J. Biol. Chem., 268, 4481–4487 (1993).

Activation of Pro-MMP-3
Pro-MMP-3 at 1.72 μM (100 μg/mL) in an MMP-3 activation buffer consisting of 5 mM Tris at pH 7.5, 5 mM $CaCl_2$, 25 mM NaCl, and 0.005% Brij-35 was activated by incubation with TPCK (N-tosyl-(L)-phenylalanine chloromethyl ketone) trypsin (1:100 w/w to pro-MMP-3) at 25° C. for 30 min. The reaction was stopped by addition of soybean trypsin inhibitor (SBTI; 5:1 w/w to trypsin concentration). This activation protocol results in formation of 45 kDa active MMP-3, which still contains the C-terminal portion of the enzyme.

Preparation of Human Recombinant Pro-gelatinase A (MMP-2)

Human Recombinant Pro-MMP-2

Human pro-gelatinase A (pro-MMP-2) was prepared using a vaccinia expression system according to the method of R. Fridman et al., J. Biol. Chem. 267, 15398–405, (1992).

Activation of Pro-MMP-2

Pro-MMP-2 at 252 mg/mL was diluted 1:5 to a final concentration of 50 mg/mL solution in an MMP-2 activation buffer consisting of 25 mM Tris at pH 7.5, 5 mM $CaCl_2$, 150 mM NaCl, and 0.005% Brij-35. p-Aminophenylmercuric acetate (APMA) was prepared at 10 mM (3.5 mg/mL) in 0.05N NaOH. The APMA solution was added at 1/20 the reaction volume for a final APMA concentration of 0.5 mM, and the enzyme was incubated at 37° C. for 30 min. Activated MMP-2 (15 mL) was dialyzed twice vs. 2 L of MMP-2 activation buffer (dialysis membranes were pretreated with a solution consisting of 0.1% BSA in MMP-2 activation buffer for 1 min., followed by extensive $H_2O$ washing). The enzyme was concentrated on Centricon concentrators (concentrators were also pretreated with a solution consisting of 0.1% BSA solution in MMP-2 activation buffer for 1 min., followed by washing with $H_2O$ then MMP-2 activation buffer) with redilution followed by reconcentration repeated twice. The enzyme was diluted to 7.5 mL (0.5 times the original volume) with MMP-2 activation buffer.

Preparation of Human Recombinant Pro-gelatinase B (MMP-9)

Human Recombinant Pro-MMP-9

Human recombinant pro-gelatinase B (pro-MMP-9) derived from U937 cDNA as described by S. M. Wilhelm et al., J. Biol. Chem., 264, 17213–17221 (1989) was expressed as the full-length form using a baculovirus protein expression system. The pro-enzyme was purified using methods previously described by M. S. Hibbs, et al., J. Biol. Chem., 260, 2493–500 (1984).

Activation of Pro-MMP-9

Pro-MMP-9 (20 $\mu$g/mL) in an MMP-9 activation buffer consisting of 50 mM Tris at pH 7.4, 150 mM NaCl, 10 mM $CaCl_2$ and 0.005% Brij-35 was activated by incubation with a 0.5 mM p-aminophenylmercuric acetate (APMA) for 3.5 h at 37° C. The enzyme was dialyzed against the same buffer to remove APMA.

Instrumentation

Hamilton Microlab AT Plus®

The MMP-profiling assay was performed robotically using a Hamilton MicroLab AT Plus®. The Hamilton was programmed to: (1) serially dilute up to 11 potential inhibitors automatically using a 2.5 mM stock solution of the inhibitor in 100% DMSO; (2) distribute substrate followed by inhibitor into a 96-well Cytofluor plate; and (3) add a single enzyme to the plate with mixing to start the reaction. Subsequent plates for each additional enzyme were prepared automatically by beginning the program at the substrate addition point, remixing the diluted inhibitors, and beginning the reaction by addition of enzyme. In this way, all MMP assays were done using the same inhibitor dilutions.

Millipore Cytofluor II

Following incubation, the plate was read on a Cytofluor II fluorometric plate reader with excitation at 340 nM and emission at 395 nM with the gain set at 80.

Buffers

Microfluorometric Reaction Buffer (MRB)

Dilutions of test compounds, enzymes and P218 substrate for the microfluorometric assay were made in microfluorometric reaction buffer (MRB) consisting of 50 mM 2-(N-morpholino)ethanesulfonic acid (MES) at pH 6.5 with 10 mM $CaCl_2$, 150 mM NaCl, 0.005 % Brij-35 and 1% DMSO.

Methods

MMP Microfluorometric Profiling Assay

The assay was done with a final P218 concentration of 6 $\mu$M, approximately 0.5 to 0.8 nM of activated MMP (one MMP per 96-well plate), and with variable inhibitor concentrations. The Hamilton MicroLab AT Plus® was programmed to serially dilute up to 11 compounds from a 2.5 mM stock (100% DMSO) to 10-times the final compound concentrations in the assay. Initially, the instrument delivered various amounts of microfluorometric reaction buffer (MRB) to a 96-tube rack of 1 mL Marsh dilution tubes. The instrument picked up 20 $\mu$L inhibitor (2.5 mM) and mixed it with buffer in row A of the Marsh rack, resulting in a 50 $\mu$M inhibitor concentration. The inhibitors were then serially diluted to 10, 5, 1, 0.2, 0.05 and 0.01 $\mu$M. Position 1 on the sample rack contained only DMSO for the "enzyme-only" wells in the assay, which resulted in no inhibitor in column 1, rows A through H. The instrument then distributed 107 $\mu$L of P218 to a single 96-well Cytofluor microtiter plate. The instrument re-mixed and loaded 14.5 $\mu$L of diluted compound from rows A to G in the Marsh rack to the corresponding rows in the microtiter plate. (Row H represented the "background" row. To this was added 39.5 $\mu$L of microfluorometric reaction buffer in place of drug or enzyme.) The reaction was started by adding 25 $\mu$L of the appropriate enzyme (at 5.86-times the final enzyme concentration) from a BSA-treated reagent reservoir to each well, excluding the Row H, the "background" row. (The enzyme reservoir was pretreated with 1% BSA in 50 mM Tris at pH 7.5 containing 150 mM NaCl for 1 h at room temperature, followed by extensive washing with $H_2O$, and drying at room temp.)

After addition and mixing of the enzyme, the plate was covered and incubated for 25 min. at 37° C. Additional enzymes were tested in the same manner by beginning the Hamilton program with the distribution of P218 substrate to the microtiter plate, followed by re-mixing and distribution of the drug from the same Marsh rack to the microtiter plate. The second (or third, etc.) MMP to be tested was then distributed from a reagent rack to the microtiter plate with mixing, prior to covering and incubation.

$IC_{50}$ Determination in Microfluorometric Assay

Data generated on the Cytofluor II was copied from an exported ".CSV" file to a master Excel spreadsheet. Data from several different MMPs (one 96-well plate per MMP) were calculated simultaneously. The percent inhibition was determined for each drug concentration by comparing the amount of hydrolysis (fluorescence units generated over 25 minutes of hydrolysis) of wells containing compound with the "enzyme only" wells in column 1. Following subtraction of background, the percent inhibition was calculated as:

$$((\text{Control values} - \text{Treated Values})/\text{Control Values}) \times 100$$

Percent inhibitions were determined for inhibitor concentrations of 5, 1, 0.5, 0.1, 0.02, 0.005 and 0.001 $\mu$M. Linear regression analysis of percent inhibition versus log inhibitor concentration was used to obtain $IC_{50}$ values.

Profiling Assay Data for Certain Compounds of the Invention

TABLE 5

MMP-Profiling Data. All $IC_{50}$ values are expressed as nM.
When "I = x %" is shown, x represents the % inhibition at 5 µM.

| Ex. # or Control Compound | MMP-3 $IC_{50}$ | MMP-9: $IC_{50}$ | MMP-2 $IC_{50}$ |
|---|---|---|---|
| B | I = 46% | 1,450 | 2,400 |
| C | I = 20% | I = 23% | I = 36% |
| D | 5,000 | 1,000 | 1,400 |
| 1 | 3,300 | 1,850 | 485 |
| 2 | 1,875 | 1,575 | 460 |
| 3 | I = 43% | 4,350 | 640 |
| E | 5,100 | 5,050 | 1,450 |
| 4 | 125 | 20 | 42 |
| 5 | 870 | 150 | 92 |
| 6 | 565 | 76 | 130 |
| 7 | 1,040 | 400 | 295 |
| 10 | 61 | 85 | 40 |
| 11 | 114 | 68 | 79 |
| 12 | 135 | 360 | 135 |
| 13 | 82 | 355 | 53 |
| F | I = 18% | I = 6% | I = 16% |
| G | I = 29% | I = 46% | I = 48% |

It can be clearly seen from the assay data of the above Table 5 that optimal MMP inhibition is achieved in compounds that have a substituent on the 4-phenyl ring of about 4–13 atoms (excluding H). If the size of the substituent is smaller, such as Br in intermediate B, or H in control D, or $CH_3O$ in control G, then the activities are low. On the other hand, if the substituent is very large, such as $C_{14}H_{29}O$ in control F, the activity is also low.

It is also clear that the exact structure of the substituent on the 4-phenyl ring can influence the selectivity of activity among the MMP's. Thus certain compounds such as the acetylenes (Examples 4–6) show higher potency with the Gelatinases (MMP-2 and MMP-9) than with Stromelysin (MMP-3), while the ethers either show broad high activity (Examples 10 and 11) or selectivity for MMP-3 and MMP-2 compared to MMP-9 (Examples 12 and 13). The ability to administer selective MMP inhibitors should result in drugs with fewer side effects for diseases such as cancers where the gelatinases play a large role and stromelysin may not be important or osteoarthritis where stromelysin is thought to play the largest role and the gelatinases are not as important.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

We claim:

1. Compounds having matrix metalloprotease inhibitory activity and the generalized formula:

wherein
$R^1$ represents a substituent independently selected from the group consisting of
$C_6$–$C_{12}$ alkyl;
$C_5$–$C_{12}$ alkoxy;
$C_5$–$C_{12}$ alkylthio;
polyether of formula $R^2O(C_2H_4O)_a$—; wherein
a is 1 or 2; and
$R^2$ is $C_1$–$C_5$ alkyl, phenyl, or benzyl; and
substituted alkynyl of formula $R^3(CH_2)_b$—C≡C—;
wherein
b is 1–10; and
$R^3$ is H—, HO—, or $R^4O$—, wherein
$R^4$ is $C_1$–$C_3$ alkyl, phenyl, or benzyl;
alkyl, phenyl, and benzyl portions of $R^1$ permissibly bearing at least one pharmaceutically-acceptable substituent;
the subscript n is 2–4;
$R^5$ represents a substituent independently selected from the group consisting of
phenyl;
imidoyl of 4–12 carbon atoms;
(3H)-benzo-1,2,3-triazin-4-on-3-yl
N-saccharinyl;
(2H)-phthalazin-1-on-2-yl;
2-benzoxazolin-2-on-3-yl;
5,5-dimethyloxazolidine-2,4-dion-3-yl; and
thiazolidine-2,4-dion-3-yl;
phenyl and benzo portions of $R^5$ permissibly bearing at least one pharmaceutically-acceptable substituent;
and pharmaceutically acceptable salts thereof.

2. A compound of claim 1 wherein $R^1$ represents an alkyl group.

3. A compound of claim 1 wherein $R^1$ represents an alkoxy or alkylthio group.

4. A compound of claim 1 wherein $R^1$ represents a polyether group.

5. A compound of claim 1 wherein $R^1$ represents a substituted alkynyl group.

6. A compound of claim 1 wherein $R^5$ represents a phenyl group.

7. A compound of claim 1 wherein $R^5$ represents an imidoyl or (3H)-benzo-1,2,3-triazin-4-on-3-yl group.

8. A compound of claim 1 wherein $R^5$ is selected from the group consisting of N-saccharinyl, (2H)-phthalazin-1-on-2-yl, 2-benzoxazolin-2-on-3-yl, 5,5-dimethyloxazolidine-2,4-dion-3-yl, and thiazolidine-2,4-dion-3-yl.

9. A compound of claim 1, selected from the group consisting of:
4-(4-(3-hydroxyprop-1-ynyl)phenyl)-4-oxo-2-(3-phenylpropyl)butyric acid,
4-(4-(hex-1-ynyl)phenyl)-4-oxo-2-(3-phenylpropyl)butyric acid,
4-(4-(6-hydroxyhex-1-ynyl)phenyl)-4-oxo-2-(3-phenylpropyl)butyric acid,
4-(4-(hex-1-ynyl)phenyl)-4-oxo-2-(2-phthalimidoethyl)butyric acid,
4-(4-(6-hydroxyhex-1-ynyl)phenyl)-4-oxo-2-(2-phthalimidoethyl)butyric acid,
4-(4-(3-hydroxyprop-1-ynyl)phenyl)-4-oxo-2-(2-phthalimidoethyl)butyric acid,
4-(4-hexylphenyl)-4-oxo-2-(2-phthalimidoethyl)butyric acid,
4-(4-(dec-1-ynyl)phenyl)-4-oxo-2-(2-phthalimidoethyl)butyric acid,
4-(4-(3-phenoxyprop-1-ynyl)phenyl)-4-oxo-2-(2-phthalimidoethyl)butyric acid,
4-(4-heptyloxyphenyl)-4-oxo-2-(2-phthalimidoethyl)butyric acid,
4-(4-hexyloxyphenyl)-4-oxo-2-(2-phthalimidoethyl)butyric acid,
4-(4-decyloxyphenyl)-4-oxo-2-(2-phthalimidoethyl)butyric acid, and 4-(4-(2-benzyloxyethoxy)phenyl)-4-oxo-2-(2-phthalimidoethyl)butyric acid.

10. A composition having matrix metalloprotease inhibitory activity, comprising a compound of claim 1 and a pharmaceutically acceptable carrier.

11. A method for treating a matrix metalloprotease-mediated condition in a mammal to achieve an effect, comprising administering to said a mammal an amount of a compound of claim 1 which is effective to treat said condition.

12. The method of claim 11 wherein said mammal is a human.

13. The method of claim 11 wherein said effect is: alleviation of osteoarthritis, rheumatoid arthritis, septic arthritis, periodontal disease, corneal ulceration, proteinuria, aneurysmal aortic disease, dystrophobic epidermolysis bullosa, conditions leading to inflammatory responses, osteopenias mediated by MMP activity, tempero mandibular joint disease, or demyelating diseases of the nervous system; retardation of tumor metastasis or degenerative cartilage loss following traumatic joint injury; reduction of coronary thrombosis from atherosclerotic plaque rupture; or improved birth control; and said amount of a compound of claim 1 is effective to inhibit the activity of at least one matrix metalloprotease in said mammal, thereby to achieve said effect.

* * * * *